US007339080B2

(12) United States Patent
Hugo et al.

(10) Patent No.: US 7,339,080 B2
(45) Date of Patent: Mar. 4, 2008

(54) METHOD FOR THE PRODUCTION OF DIAMINOXYLENE BY CONTINUOUS HYDROGENATION OF LIQUID PHTHALONITRILE

(75) Inventors: Randolf Hugo, Dirmstein (DE); Kirsten Wenz, Mannheim (DE); Rolf Wambsganβ, Landau (DE); Sabine Jourdan, Mannheim (DE); Thomas Preiss, Weisenheim Am Sand (DE)

(73) Assignee: BASF Aktiengesellschaft (DE)

( * ) Notice: Subject to any disclaimer, the term of this patent is extended or adjusted under 35 U.S.C. 154(b) by 31 days.

(21) Appl. No.: 10/570,099

(22) PCT Filed: Sep. 9, 2004

(86) PCT No.: PCT/EP2004/010063

§ 371 (c)(1),
(2), (4) Date: Mar. 1, 2006

(87) PCT Pub. No.: WO2005/026099

PCT Pub. Date: Mar. 24, 2005

(65) Prior Publication Data

US 2006/0258889 A1 Nov. 16, 2006

(30) Foreign Application Priority Data

Sep. 10, 2003 (DE) ................................ 103 41 612
Sep. 10, 2003 (DE) ................................ 103 41 613
Sep. 10, 2003 (DE) ................................ 103 41 614
Sep. 10, 2003 (DE) ................................ 103 41 615
Sep. 10, 2003 (DE) ................................ 103 41 632
Sep. 10, 2003 (DE) ................................ 103 41 633
Sep. 2, 2004 (DE) ...................... 10 2004 042 947

(51) Int. Cl.
*C07C 209/00* (2006.01)

(52) U.S. Cl. ...................................................... 564/415

(58) Field of Classification Search ..................... None
See application file for complete search history.

(56) References Cited

U.S. PATENT DOCUMENTS 3,069,469 A 12/1962 Wilkes
3,574,754 A 4/1971 Specken
4,482,741 A 11/1984 Kurek
5,371,292 A 12/1994 Merger et al.
5,530,127 A 6/1996 Reif et al.
5,696,048 A 12/1997 Breitscheidel et al.
6,297,394 B1 10/2001 Voit et al.
6,476,267 B1 11/2002 Fuchigami et al.

FOREIGN PATENT DOCUMENTS

| | | |
|---|---|---|
| CN | 1285236 | 2/2001 |
| CN | 1285343 | 2/2001 |
| DE | 902 616 | 1/1954 |
| DE | 1 074 592 | 2/1960 |
| DE | 1 119 285 | 12/1961 |
| DE | 1 259 899 | 2/1968 |
| DE | 2 164 169 | 7/1972 |
| DE | 102004042954 | 9/2004 |
| DE | 103 41 612 | 4/2005 |
| DE | 103 41 613 | 4/2005 |
| DE | 103 41 614 | 4/2005 |
| DE | 103 41 615 | 4/2005 |
| DE | 103 41 632 | 4/2005 |
| DE | 103 41 633 | 4/2005 |
| EP | 0 449 089 | 10/1991 |
| EP | 0 696 572 | 2/1996 |
| EP | 0 742 045 | 11/1996 |
| EP | 0 963 975 | 12/1999 |
| EP | 1 193 244 | 4/2002 |
| EP | 1 193 247 | 4/2002 |
| EP | 1 262 232 | 12/2002 |
| EP | 1 279 661 | 1/2003 |
| GB | 852972 | 11/1960 |
| GB | 1143390 | 2/1969 |
| JP | 2003-327563 | 11/2003 |
| WO | WO-99/44984 | 9/1999 |
| WO | WO-00/46179 | 8/2000 |
| WO | WO-02-205980 | 7/2002 |

*Primary Examiner*—Samuel Barts

(57) ABSTRACT

A process for preparing xylylenediamine by continuously hydrogenating liquid phthalonitrile over a heterogeneous catalyst in the presence of liquid ammonia in a reactor, which comprises mixing a stream of a phthalonitrile melt in liquid form by means of a mixer unit with a stream of liquid ammonia and conducting the liquid mixture into the hydrogenation reactor.

24 Claims, 3 Drawing Sheets

Scheme:

Mixer nozzle
heat carrier medium
$NH_3$, liquid
PN melt
solution of PN in $NH_3$
heat carrier medium radial feed
$NH_3$ (liquid)
or
$NH_3$ (liquid)
$NH_3$ (liquid)
tangential feed
$NH_3$ (liquid)
or
$NH_3$ (liquid)
$NH_3$ (liquid)

Mixer unit for PN melt and ammonia (liquid)

METHOD FOR THE PRODUCTION OF DIAMINOXYLENE BY CONTINUOUS HYDROGENATION OF LIQUID PHTHALONITRILE

RELATED APPLICATIONS

This application is a national stage application (under 35 U.S.C. 371) of PCT/EP2004/010063 filed Sep. 9, 2004 which claims benefit to German applications 103 41 612.9, 103 41 633.1, 103 41 632.3, 103 41 615.3, 103 41 613.7, 103 41 614.5 all filed on Sep. 10, 2003, and German application 10 2004 042 947.2 filed Sep. 2, 2004.

DESCRIPTION

The present invention relates to a process for preparing xylylenediamine by continuously hydrogenating liquid phthalonitrile over a heterogeneous catalyst in the presence of liquid ammonia in a reactor.

Xylylenediamine (bis(aminomethyl)benzene) is a useful starting material, for example, for the synthesis of polyamides, epoxy hardeners or as an intermediate for preparing isocyanates.

The term "xylylenediamine" (XDA) comprises the three isomers, ortho-xylylenediamine, meta-xylylenediamine (MXDA) and para-xylylenediamine.

The term "phthalonitrile" (PN) comprises the three isomers, 1,2-dicyanobenzene=o-phthalonitrile, 1,3-dicyanobenzene=isophthalonitrile=IPN and 1,4-dicyanobenzene=terephthalonitrile.

The phthalonitriles are solids (for example, isophthalonitrile (IPN) melts at 161° C.) and have relatively poor solubilities in organic solvents.

The two-stage synthesis of xylylenediamine by ammoxidation of xylene and subsequent hydrogenation of the resulting phthalonitrile is known. Unconverted dinitriles are very difficult to remove distillatively from the XDA.

U.S. Pat. No. 4,482,741 (UOP Inc.) describes the hydrogenation of PN in the presence of ammonia, a specific catalyst and XDA as a solvent.

In MXDA, the solubility of IPN at 70° C. is approx. 20% by weight.

EP-A2-1 193 247 and EP-A1-1 279 661 (both Mitsubishi Gas Chem. Comp.) relate, respectively, to a process for purifying isophthalonitrile (IPN) and to a process for preparing pure XDA.

EP-A2-1 193 244 (Mitsubishi Gas Chem. Comp.) describes a process for preparing XDA by hydrogenating phthalonitrile which is synthesized in a preceding stage by ammoxidation of xylene, wherein the vaporous product of the ammoxidation stage is contacted directly with a liquid organic solvent (quench) and the resulting quench solution or suspension is fed to the hydrogenation.

Preferred organic solvents are $C_6$-$C_{12}$ aromatic hydrocarbons, such as xylene and pseudocumene (column 6, paragraphs [0027] and [0028]).

U.S. Pat. No. 3,069,469 (California Research Corp.) teaches aromatic hydrocarbons, xylene, dioxane and aliphatic alcohols as solvents for the hydrogenation of aromatic nitrites such as PN.

DE-A-21 64 169 (Mitsubishi Gas Chemical Co., Inc.) describes, on page 6, last paragraph, the hydrogenation of IPN to meta-XDA in the presence of an Ni and/or Co catalyst in ammonia as a solvent.

GB-A-852,972 (equivalent: DE-A-11 19 285) (BASF AG) discloses the use of ammonia and XDA as a solvent in the hydrogenation of PN. The reactant solution is prepared starting from solid PN in an extra step in a separate vessel (cf. page 2, lines 119-120).

JP-A-2003-327563 (Mitsubishi Gas Chem. Co., Inc.) relates to a process for the fixed bed hydrogenation of aromatic dinitriles which are used as 1-10% by weight solutions.

The six German patent applications having the reference numbers 10341615.3, 10341632.3, 10341614.5, 10341633.1, 10341612.9 and 10341613.7 (BASF AG) of Sep. 10, 2003 each relate to processes for preparing XDA.

German patent application No. 102004042954.5 of Sep. 2, 2004 (BASF AG) relates to a process for preparing XDA by continuously hydrogenating liquid phthalonitrile over a heterogeneous catalyst in the presence of liquid ammonia in a reactor, in which a portion of the reactor effluent is recycled as a liquid circulation stream continuously to the reactor inlet (circulation mode), wherein a stream of a phthalonitrile melt is conducted in liquid form by means of a mixer unit into the circulation stream around the hydrogenation reactor, the phthalonitrile conversion in the reactor on single pass being greater than 99%, and the circulation stream consisting to an extent of greater than 93% by weight of liquid ammonia and xylylenediamine and not comprising any further solvent for phthalonitrile.

In the different processes for preparing phthalonitrile, it is obtained as a solid or dissolved in a solvent, for example pseudocumene, or as a melt. The handling of solids is typically difficult and laborious. Owing to the low solubility of phthalonitrile in solvents such as o-xylene, m-xylene, p-xylene, pseudocumene, mesitylene, ethylbenzene or methylpyridine, the further processing in a solvent requires very large amounts of solvent which generally have to be removed distillatively after the hydrogenation, which requires large apparatus and a high energy input corresponding to the large mass flow rates. Alternatively, an extraction of the PN with water with subsequent distillation is possible. Here too, the energy input is large, since the water has to be distilled off and the solvent regenerated, at least partially.

It is an object of the present invention to find an improved economically viable process for preparing xylylenediamine, especially meta-xylylenediamine, with high selectivity, yield and space-time yield (STY), which enables reduced-scale and/or fewer apparatuses and machines at throughputs comparable to the prior art owing to reduced streams, especially solvent streams, including recycle streams.

Accordingly, a process has been found for preparing xylylenediamine by continuously hydrogenating liquid phthalonitrile over a heterogeneous catalyst in the presence of liquid ammonia in a reactor, which comprises mixing a stream of a phthalonitrile melt in liquid form by means of a mixer unit with a stream of liquid ammonia and conducting the liquid mixture into the hydrogenation reactor.

The process according to the invention preferably finds use for preparing meta-xylylenediamine (MXDA) by hydrogenating isophthalonitrile (IPN), which has been synthesized in particular in a preceding stage by ammoxidation of meta-xylene.

The molten phthalonitrile may come, for example, from a quench connected downstream of an ammoxidation, an evaporative concentration stage or a distillation column, and the phthalonitrile may, for example, in each case be removed as a melt via the bottom of these thermal separation apparatuses, as described, for example, in German patent application no. 10341633.1 of Sep. 10, 2003 (BASF AG).

Alternatively, it is also possible in the process according to the invention to use molten PN present beforehand as a solid. The melting may be effected, for example, by means of an extruder.

The advantage of metering the PN as a melt into the liquid ammonia is that the phthalonitrile is present already directly after the mixing in diluted form and at distinctly reduced temperature before it comes into contact with xylylenediamine (from the optional circulation system or formed in the hydrogenation reactor), which can substantially suppress an undesired reaction between nitrile and product. Moreover, the melt can be metered at a pressure which is less than the reactor pressure, which allows a less expensive melt pump to be used. The solution may then subsequently be compressed to the desired reactor pressure.

The feeding and dissolution of the phthalonitrile melt in liquid ammonia requires a mixer unit, preferably a mixer nozzle or a mixer vessel.

A mixer nozzle can be realized in the simplest case by a pipeline T-piece. The nozzle mouth preferably has a narrowing.

When using a mixer nozzle, the streams are fed separately and are mixed and homogenized in the attached tube on the basis of the prevailing turbulence. Advantageously, a static mixer may additionally be connected downstream. However, no additional apparatus, for instance a stirred tank for the dissolution of (solid or liquid) phthalonitrile in a solvent, is required.

Preference is given to heating the mixer unit at the point of the phthalonitrile supply into the stream of liquid ammonia to a temperature in the range from 1 to 40° C., preferably in the range from 5 to 25° C., above the melting point of the phthalonitrile used.

Preference is given to supplying the PN virtually at an absolute pressure between 15 bar and the reactor pressure. The minimum pressure arises from the particularly preferred boundary condition that no evaporation occurs in the course of mixing and at the mixing temperature established, but rather the mixture remains liquid. It is thus dependent upon the starting temperature and the ratio of the components to be mixed. Mixing at low pressure, for example 40 bar, offers the advantage that the melt pump does not have to be designed for the distinctly higher reactor pressure. However, the PN solution in ammonia still has in this case to be compressed to the reactor pressure by means of a high pressure pump, albeit one of simple construction. It is possible to dispense with the latter if the mixing is effected actually at reactor pressure. Which variant is to be preferred depends upon availability of the apparatus and machines, and also upon economic standpoints.

DETAILED DESCRIPTION

Particular preference is given to spraying the liquid phthalonitrile by means of a mixer nozzle as the mixer unit into the stream of liquid ammonia.

Figure 2:
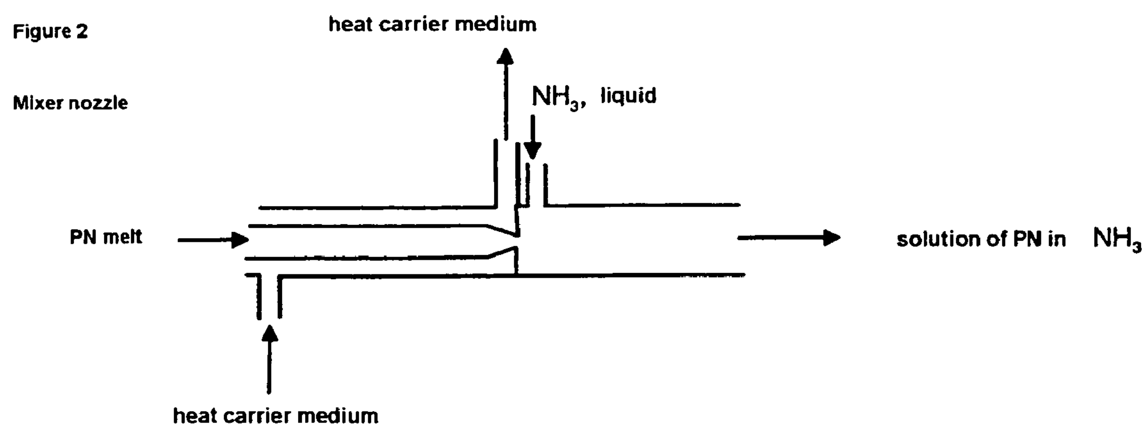
FIG. 2 schematically illustrates a mixer nozzle in accordance with this invention.

A preferred embodiment of the mixer nozzle is shown in FIG. 2 in the appendix. The mixer nozzle may be heated, for example, with steam, heat carrier oil or else electrically.

Figure 3:
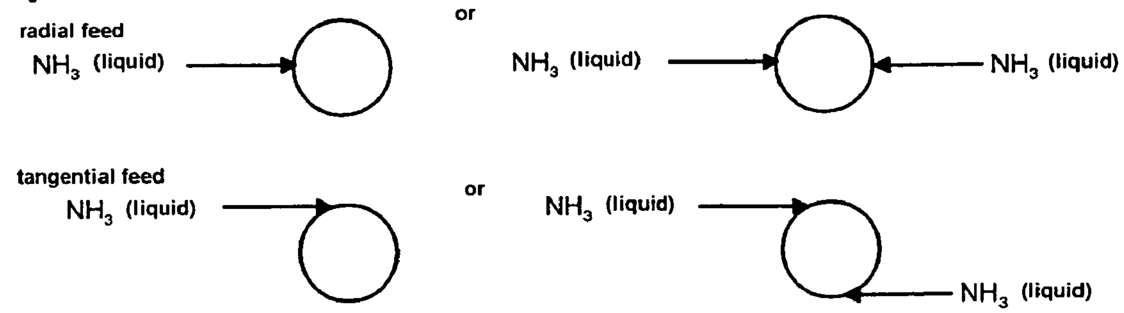
FIG. 3 schematically illustrates the feeding of liquid ammonia in accordance with this invention.

The liquid ammonia may be fed via one or more radially or tangentially mounted nozzles, for example as shown in FIG. 3.

It is important that there is a localized high flow rate (high impulse stream and turbulence), so that rapid mixing (homogenization) occurs. In the case of laminar flow, the mass transfer is insufficient for homogenization and the flows are only mixed inadequately (streaking).

Suitable mixer nozzles are described, for example, in Ullmann's Encyclopedia of Industrial Chemistry, 5th edition, Vol. B4, pages 565-569.

Figure 4:
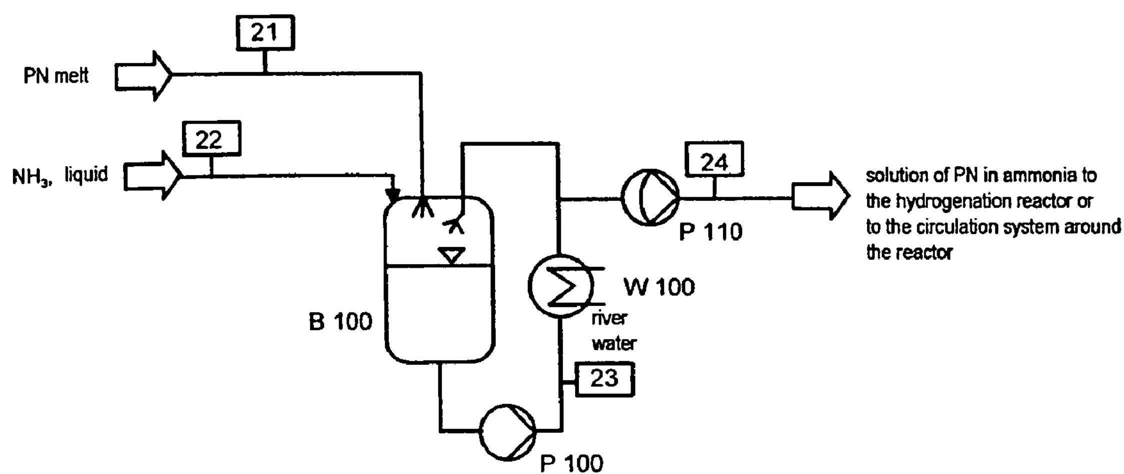
FIG. 4 schematically illustrates a mixer u it in the form of a mixer vessel with a circulation system in accordance with this invention.

A further particularly preferred mixer unit is a mixer vessel with circulation system, as shown, for example, in FIG. 4.

The PN melt (stream [21]) and the liquid ammonia (stream [22]) are fed separately to vessel B 100. PN and the solution from the circulation system (stream [23]) are each sprayed (atomized) with the aid of nozzles. For each stream, one or else more nozzles may be used. The liquid ammonia may likewise be sprayed. If the circulation system around the mixer vessel is dispensed with, ammonia is sprayed instead of the solution. The solution from the circulation system or the liquid ammonia are preferably sprayed such that a majority of gas space is covered. In particular, the solution or the ammonia is sprayed over the entire cross-sectional area, so that some of the solution or some of the liquid ammonia runs down the vessel walls and forms a liquid film. This prevents solid deposits. The PN is likewise sprayed, but preferably within a narrower spray cone which is substantially within the solution or ammonia spray cone. Advantageously, this can be realized, for example, by the PN nozzle being mounted centrally and, for example, three or more nozzles for solution or ammonia being arranged around it. The small PN droplets mix and dissolve spontaneously in the ammonia or in the solution. The mixture is conveyed from the mixer vessel with the pump P 100 and can be cooled to the desired temperature in a heat transferrer W 100. Subsequently, the mixture is compressed to reactor pressure with the pump P 110 (stream [24]). Advantageously, a portion of the mixture downstream of the reactor is conveyed back to the mixer vessel and sprayed by means of nozzles. However, it is also possible to dispense with the circulation system. In that case, stream [23] is equal to stream [24]. The operating pressure of the vessel is dependent upon the process conditions, especially upon the temperature. At a given feed temperature of the fresh ammonia (stream [22]) and of the PN melt (stream [21]), variation of the circulation stream and adjustment of the temperature of the circulation stream downstream of the cooler W 100 allows the mixing temperature in the vessel to be selected within certain limits, especially taking into account the temperature-dependent solubility of PN in ammonia. This results in the appropriate vapor pressure being established over the solution in the gas space. If appropriate, inert gas, for example nitrogen, may also be present in the gas space. Advantageously, the pressure in the vessel B 100 is not more than 25 bar, so that inexpensive apparatus and machines can be used. The high-pressure pump P 110 then compresses the solution to the reactor pressure for the hydrogenation.

Depending on whether the hydrogenation is conducted with or without circulation system around the hydrogenation reactor, the stream [24] can be conducted to the reactor or into the circulation system around the reactor.

In a preferred embodiment of the process according to the invention, a portion of the reactor effluent is recycled as a liquid circulation stream continuously to the reactor inlet (circulation mode) and the liquid mixture of ammonia and phthalonitrile is fed into the circulation stream around the hydrogenation reactor, the circulation stream consisting to an extent of greater than 93% by weight of liquid ammonia and xylylenediamine.

Employment of a circulation stream allows the phthalonitrile solution to be diluted further or the amount of fresh ammonia to be reduced. In any case, a high ammonia concentration is attained in the reactor, which in turn has a favorable effect on the selectivity.

In an advantageous embodiment of the process according to the invention, the reactor mixture furthermore does not comprise any further solvent for phthalonitrile.

The phthalonitrile conversion in the hydrogenation reactor on single pass is preferably greater than 99%, particularly greater than 99.5%, very particularly greater than 99.9%, in particular greater than 99.95%, very particularly greater than 99.97%. In the hydrogenation reactor, appropriate setting of the reaction conditions (pressure, temperature, molar ratios of PN, $NH_3$ and $H_2$, catalyst, mass flow rates, residence time in the reactor) allows virtually full conversion to be attained.

The liquid circulation stream around the hydrogenation reactor (in the process variant with circulation mode) consists preferably to an extent of greater than 94% by weight, in particular greater than 95% by weight, very particularly greater than 96% by weight, of liquid ammonia and xylylenediamine; the remainder is formed by secondary components.

Secondary components in the liquid circulation stream around the hydrogenation reactor may be by-products formed in the reaction, and also dissolved gases and secondary components fed with the phthalonitrile, but not a further solvent, for example organic solvent, for phthalonitrile.

The circulation stream around the hydrogenation reactor (in the process variant with circulation mode) comprises preferably in the range from 25 to 90% by weight, particularly from 30 to 70% by weight, in particular from 45 to 60% by weight, of liquid ammonia.

The portion of the liquid effluent which (in the process variant with circulation mode) is recycled as a circulation stream continuously to the reactor inlet makes up preferably from 20 to 95% by weight, particularly from 50 to 92% by weight, in particular from 75 to 90% by weight, of the overall liquid reactor effluent.

The weight ratio of phthalonitrile/ammonia feed stream to circulation stream around the hydrogenation reactor (in the process variant with circulation mode) is preferably in the range from 0.05 to 5, particularly in the range from 0.1 to 2.0, in particular in the range from 0.15 to 1.0.

The reaction temperature is preferably in the range from 40 to 150° C., more preferably from 60 to 135° C., in particular from 70 to 130° C.

The amount of ammonia, the amount of the circulation stream which is optionally present around the hydrogenation reactor (in the process variant with circulation mode) and the reactor feed temperature are adjusted such that the reactor outlet temperature does not exceed the desired maximum value (for example 130° C.), since by-products are formed to an enhanced degree with increasing temperature. The reactor feed temperature is adjusted in such a way (for example by an additional heat carrier or, preferably, by suitably adjusting the temperature of the streams to be mixed), that the reaction proceeds sufficiently rapidly and full conversion is attained. Variation of the circulation mass flow rate around the hydrogenation reactor and fresh mass flow rate of ammonia thus makes it possible to adjust both inlet and outlet temperature of the reactor and adjust them optimally to the reactions proceeding, and thus to optimize the XDA yield.

The hydrogenation is carried out preferably at an absolute pressure in the range from 100 to 300 bar, in particular from 120 to 220 bar, very particularly from 150 to 200 bar.

For the hydrogenation, the catalysts and reactors known to those skilled in the art (especially tubular reactors or tube bundle reactors; fixed bed or suspension mode) may be employed.

In the fixed bed catalyst method, both the liquid phase and the trickle mode are possible. Preference is given to trickle mode.

Preference is given to operating the reactor adiabatically, while the heat of reaction which arises is removed via a cooler installed in the circulation system, and also optionally with the cycle gas used. This additionally increases the selectivity of the reaction by the further suppression of by-products. Alternatively, it is also possible to use a cooled reactor, for example a tube bundle reactor.

Preference is given to catalysts which comprise cobalt and/or nickel and/or iron, as an unsupported catalyst or on an inert support.

Particular preference is given to carrying out the hydrogenation over a manganese-doped unsupported cobalt catalyst.

Suitable catalysts are for example, Raney nickel, Raney cobalt, unsupported cobalt catalyst, titanium-doped cobalt on support (JP-A-2002 205980), Ni on $SiO_2$ support (WO-A-2000/046179), Co/Ti/Pd on $SiO_2$ support (CN-A-1 285 343, CN-A-1 285 236) and nickel and/or cobalt on zirconium dioxide support (EP-A1-1 262 232).

Examples of further suitable catalysts can be found, for example, in the applications GB-A-852,972 (equivalent: DE-A-11 19 285) (BASF AG), DE-A-12 59 899 (BASF AG) and the U.S. Pat. No. 3,069,469 (California Research Corp.) and U.S. Pat. No. 4,482,741 (UOP Inc.).

Particularly preferred catalysts are the unsupported cobalt catalysts doped with Mn, P and alkali metal (Li, Na, K, Rb, Cs) which are disclosed in EP-A1-742 045 (BASF AG). Before the reduction with hydrogen, the catalytically active composition of these catalysts consists of from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, calculated in each case as the oxide.

Further suitable catalysts are the catalysts disclosed in EP-A-963 975 (BASF AG), whose catalytically active composition before treatment with hydrogen comprises from 22 to 40% by weight of $ZrO_2$, from 1 to 30% by weight of oxygen compounds of copper, calculated as CuO, from 15 to 50% by weight of oxygen compounds of nickel, calculated as NiO, where the molar Ni:Cu ratio is greater than 1, from 15 to 50% by weight of oxygen compounds of cobalt, calculated as CoO, from 0 to 10% by weight of oxygen compounds of aluminum and/or manganese, calculated as $Al_2O_3$ or $MnO_2$, and no oxygen compounds of molybdenum, for example the catalyst A disclosed in loc. cit., page 17, with the composition of 33% by weight of Zr, calculated as $ZrO_2$, 28% by weight of Ni, calculated as NiO, 11% by weight of Cu, calculated as CuO and 28% by weight of Co, calculated as CoO, the catalysts disclosed in EP-A-696 572 (BASF AG), whose catalytically active composition before the reduction with hydrogen comprises from 20 to 85% by weight of $ZrO_2$, from 1 to 30% by weight of oxygen compounds of copper, calculated as CuO, from 30 to 70% by weight of oxygen compounds of nickel, calculated as NiO, from 0.1 to 5% by weight of oxygen compounds of molybdenum, calculated as $MoO_3$, and from 0 to 10% by weight of oxygen compounds of aluminum and/or manganese, calculated as $Al_2O_3$ or $MnO_2$, for example the catalyst disclosed in loc. cit., page 8, with the composition of 31.5% by weight of $ZrO_2$, 50% by weight of NiO, 17% by weight of CuO and 1.5% by weight of $MoO_3$, and the catalysts described in WO-A-99/44984 (BASF AG) and comprising (a) iron or a compound based on iron or mixtures thereof, (b) from 0.001 to 0.3% by weight based on (a) of a promoter based on 2, 3, 4 or 5 elements selected from the group of Al, Si, Zr, Ti, V, (c) from 0 to 0.3% by weight based on (a) of a compound based on an alkali metal and/or alkaline earth metal, and (d) from 0.001 to 1% by weight based on (a) of manganese.

Figure 1:
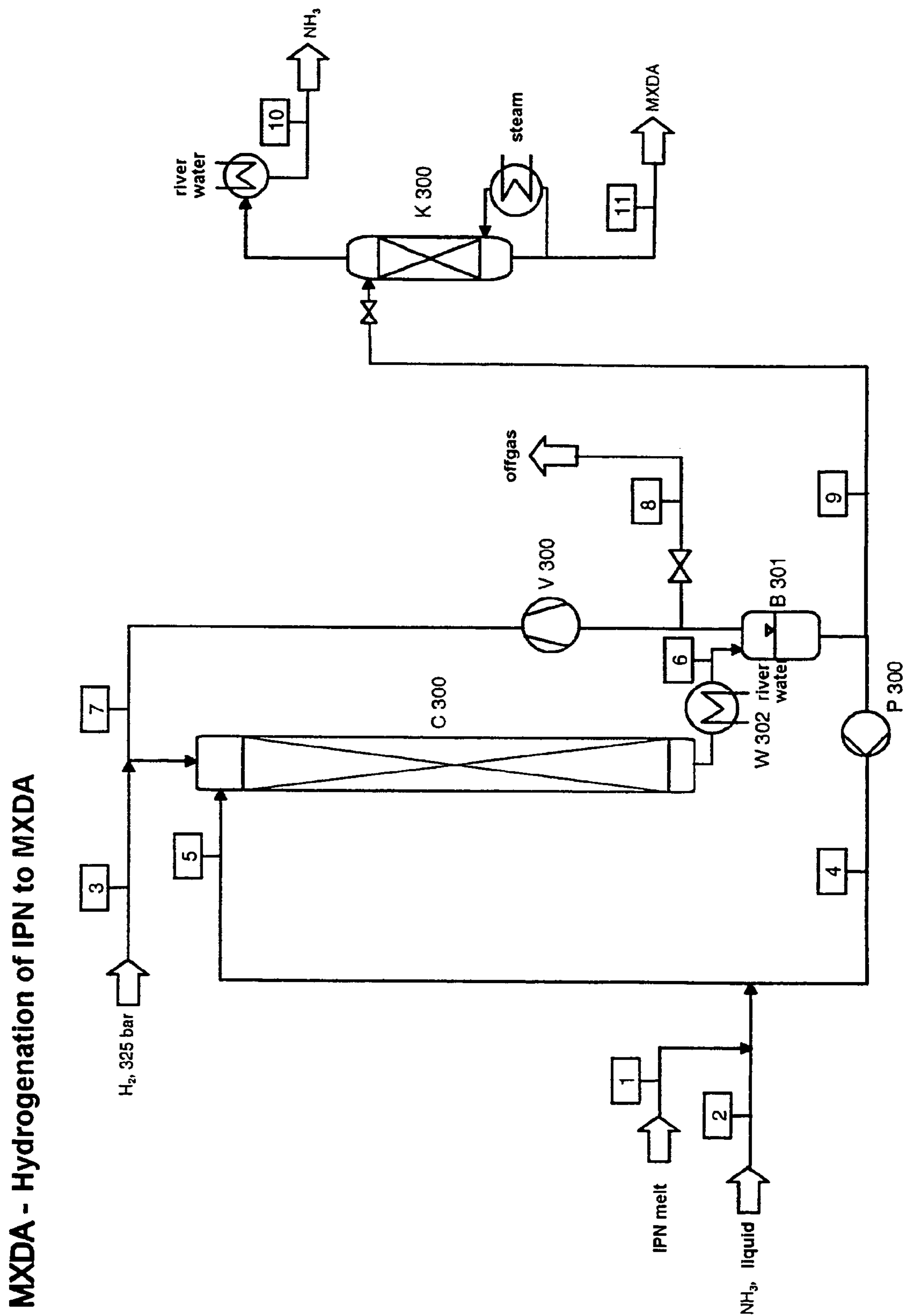
FIG. 1 schematically illustrates equipment for practicing the process of this invention.

The process according to the invention can be performed, for example, as follows:

FIG. 1 shows one possible arrangement of the hydrogenation reactor including the optional circulation system and a heat transferee. The phthalonitrile melt is fed as a stream [1] and mixed with the liquid ammonia [2]. The mixture is either mixed with the circulation system [4] which is optionally present or fed directly to the reactor. For better mixing with the circulation system, it is possible to use, for example, a static mixer. Hydrogen and any cycle gas may be heated to the desired reactor feed temperature by means of an optional heat transferee. Gas and liquid may be fed to the reactor together or, preferably, separately. Preference is given to setting the temperature of the streams to be mixed by means of heat transferers in such a way that no further heat transferer is required downstream of the mixing point. In the reactor, the hydrogenation proceeds virtually quantitatively, so that virtually no phthalonitrile is present any longer in the reaction effluent. The reaction effluent may then be cooled, and gas and liquid are separated under pressure in a high-pressure separator. In liquid circulation mode, a portion of the liquid from the reaction effluent without workup is circulated (stream [4]). Otherwise, the reaction effluent is fed to workup (stream [9]). A portion of the gas is discharged in order to prevent the accumulation of inerts (CO, $N_2$, $CH_4$, noble gases, etc.). The majority of the gas is recycled to the reactor inlet via a compressor. In the event of not too high a pressure drop in the reactor, it is preferably also possible for this purpose to use an ejector jet nozzle ("waterjet pump"). Overall, the amount of cycle gas may be varied within wide ranges, for instance from several times the amount of fresh gas down to zero (method without cycle gas). The cycle gas mode is favorable in order to load the reactor on the gas side sufficiently for good mass transfer and in order to provide a sufficient entrainment stream for inert gases, in order to be able to discharge them at the reactor outlet. In addition, a portion of the heat of reaction may be removed with the gas stream. With increasing temperature, an increasing amount of ammonia evaporates, which further enhances the cooling effect of the cycle gas. The reaction effluent (stream [9]) is then fed initially to a pressure distillation, in which liquid ammonia is obtained overhead (stream [10]) and substantially ammonia-free, crude xylylenediamine is obtained via the bottom (stream [11]), and the ammonia can be fed back to the hydrogenation stage in condensed form. The crude xylylenediamine is further purified, for example, by distillation.

In the process according to the invention, the larger the circulation stream (in the process variant with circulation mode) is, the larger the weight ratio of the fresh feeds of dinitrile and ammonia (for example, according to FIG. 1, the ratio of stream [1] to stream [2]) selected may be. The lower limit of the mass flow of ammonia results from the solubility of PN in liquid ammonia at the given temperature (for example, the solubility of IPN in $NH_3$ at 40° C. is approx. 45% by weight).

The feedstock weight ratio of dinitrile to ammonia is preferably from 1:0.5 to 1:10, preferentially from 1:0.6 to 1:5, more preferably from 1:0.9 to 1:3.5.

In the method without circulation liquid around the hydrogenation reactor, the feedstock weight ratio of dinitrile to ammonia is preferably from 1:2.5 to 1:100, preferably from 1:4 to 1:13, more preferably from 1:5 to 1:10.

Isolation of the XDA:

After the hydrogenation, the ammonia used is removed, for example distilled off.

Preference is given to purifying the xylylenediamine by distilling off relatively low-boiling by-products (at the same pressure) overhead and distillatively removing relatively high-boiling impurities via the bottom.

Particular preference is given to the method in which, after the hydrogenation, the ammonia and any low-boiling by-products are distilled off overhead and then relatively high-boiling impurities are removed from the xylylenediamine distillatively via the bottom.

In a particular embodiment, the removal of relatively low- and relatively high-boiling by-products may also be effected in a side draw or dividing wall column, in which pure xylylenediamine is obtained via a liquid or gaseous side draw.

Depending on the desired purity, the product (XDA) is additionally extracted with an organic solvent, preferably an aliphatic hydrocarbon, in particular a cycloaliphatic hydrocarbon, very particularly cyclohexane or methylcyclohexane.

This purification by extraction may be effected, for example, according to DE-A-1 074 592 (BASF AG).

EXAMPLES

Example 1

90 g/h of molten IPN (commercial, chip-form IPN which has been melted by heating to approx. 170° C.) was dissolved with 90 g/h of fresh ammonia by means of a pipeline T-piece. This corresponds to the solubility at 45° C. The calculated mixing temperature in the event of ideal mixing is 74° C. when ammonia is metered at 25° C. The boiling pressure is 32.3 bar (abs.), i.e. the mixture remains liquid above this pressure and no evaporation of ammonia takes place. The solution was conducted into a circulation stream (approx. 1000 g/h) consisting of the liquid recycle stream of the reactor effluent. The resulting reaction mixture was hydrogenated continuously in a tubular reactor over an unsupported cobalt catalyst at 90° C. and 200 bar. The removed portion of the reactor effluent was freed of the majority of the amount of ammonia in an ammonia column and analyzed by GC. At full conversion of the IPN used (i.e. conversion greater than 99.95%; no reactants detectable by GC), the selectivity was 93%.

In subsequent distillation steps, residual ammonia and low-boiling secondary components were first removed. After removing the high-boiling impurities via the bottom, MXDA was obtained as the top product of a distillation column in a purity of more than 99.9% by weight.

Example 2

90 g/h of molten IPN (commercial, chip-form IPN which has been melted by heating to approx. 170° C.) was dissolved with 270 g/h of fresh ammonia by means of a pipeline T-piece. The calculated mixing temperature in the event of ideal mixing is 52° C. when ammonia is metered at 25° C. The boiling pressure is 20.5 bar (abs.), i.e. the mixture remains liquid above this pressure and no evaporation of ammonia takes place. The solution was conducted into a circulation stream (approx. 900 g/h) consisting of the liquid recycle stream of the reactor effluent. The resulting reaction mixture was hydrogenated continuously in a tubular reactor over an unsupported cobalt catalyst at 90° C. and 200 bar. The removed portion of the reactor effluent was freed of the majority of the amount of ammonia in an ammonia column and analyzed by GC. At full conversion of the IPN used, the selectivity was 95%.

In subsequent distillation steps, residual ammonia and low-boiling secondary components were first removed. After removing the high-boiling impurities via the bottom, MXDA was obtained as the top product of a distillation column in a purity of more than 99.9% by weight.

Example 3

90 g/h of molten IPN (commercial, chip-form IPN which has been melted by heating to approx. 170° C.) was dissolved with 600 g/h of fresh ammonia by means of a pipeline T-piece. The calculated mixing temperature in the event of ideal mixing is 41° C. when ammonia is metered at 25° C. The boiling pressure is 16 bar (abs.), i.e. the mixture remains liquid above this pressure and no evaporation of ammonia takes place. The resulting reaction mixture was hydrogenated continuously in a tubular reactor over an unsupported cobalt catalyst at 90° C. and 200 bar. The removed portion of the reactor effluent was freed of the majority of the amount of ammonia in an ammonia column and analyzed by GC. At full conversion of the IPN used, the selectivity was 93%.

In subsequent distillation steps, residual ammonia and low-boiling secondary components were first removed. After removing the high-boiling impurities via the bottom, MXDA was obtained as the top product of a distillation column in a purity of more than 99.9% by weight.

What is claimed is:

1. A process for preparing xylylenediamine by continuously hydrogenating liquid phthalonitrile over a heterogeneous catalyst in the presence of liquid ammonia in a reactor, which comprises mixing a stream of a phthalonitrile melt in liquid form by means of a mixer unit with a stream of liquid ammonia and conducting the liquid mixture into the hydrogenation reactor.

2. The process according to claim 1 for preparing meta-xylylenediamine by hydrogenating isophthalonitrile.

3. The process according to claim 1, wherein the mixer unit is heated at the point of the phthalonitrile supply into the stream of liquid ammonia to a temperature in the range from 1 to 40° C. above the melting point of the phthalonitrile used.

4. The process according to claim 1, wherein the liquid phthalonitrile is sprayed into the stream of liquid ammonia by means of a mixer nozzle as the mixer unit.

5. The process according to claim 1, wherein the liquid phthalonitrile and liquid ammonia or a solution of phthalonitrile in ammonia are atomized in a mixer vessel as the mixer unit.

6. The process according to claim 1, wherein a portion of the reactor effluent is recycled as a liquid circulation stream continuously to the reactor inlet (circulation mode) and the liquid mixture of ammonia and phthalonitrile is fed into the circulation stream around the hydrogenation reactor, the circulation stream consisting to an extent of greater than 93% by weight of liquid ammonia and xylylenediamine.

7. The process according to claim 1, wherein the reactor mixture does not comprise any further solvent for phthalonitrile.

8. The process according to claim 1, wherein the phthalonitrile conversion in the hydrogenation reactor on single pass is greater than 99%.

9. The process according to claim 1, wherein the phthalonitrile conversion in the hydrogenation reactor on single pass is greater than 99.5%.

10. The process according to claim 6, wherein the circulation stream consists to an extent of greater than 94% by weight of liquid ammonia and xylylenediamine.

11. The process according to claim 6, wherein the circulation stream around the hydrogenation reactor comprises in the range from 25 to 90% by weight of liquid ammonia.

12. The process according to claim 6, wherein the portion of the liquid reactor effluent which is recycled as the circulation stream continuously to the reactor inlet makes up from 20 to 95% by weight of the overall liquid reactor effluent.

13. The process according to claim 6, wherein the weight ratio of phthalonitrile/ammonia feed stream to circulation stream around the hydrogenation reactor is in the range from 0.05 to 5.

14. The process according to claim 1, wherein the hydrogenation is carried out at a temperature in the range from 40 to 150° C.

15. The process according to claim 1, wherein the hydrogenation is carried out at an absolute pressure in the range from 100 to 300 bar.

16. The process according to claim 1, wherein the hydrogenation is carried out over a catalyst comprising Ni, Co and/or Fe, as an unsupported catalyst or on an inert support.

17. The process according to claim 1, wherein the hydrogenation is carried out over a manganese-doped unsupported cobalt catalyst.

18. The process according to claim 1, wherein the catalyst is disposed as a fixed bed in a tubular reactor or tube bundle reactor.

19. The process according to claim 18, wherein the reactor is operated in trickle mode.

20. The process according to claim 1, wherein the reactor is operated adiabatically.

21. The process according to claim 6, wherein heat is withdrawn from the circulation stream around the hydrogenation reactor in a cooler.

22. The process according to claim 1, wherein the xylylenediamine is purified after the hydrogenation by distilling off the ammonia and also any relatively low-boiling by-products overhead and distillatively removing relatively high-boiling impurities via the bottom.

23. The process according to claim 22, wherein the xylylenediamine is extracted after the distillation with an organic solvent for further purification.

24. The process according to claim 23, wherein cyclohexane or methylcyclohexane are used for the extraction.

* * * * *